(12) United States Patent
Suchkov et al.

(10) Patent No.: US 11,944,383 B2
(45) Date of Patent: Apr. 2, 2024

(54) APPARATUS AND METHOD FOR DETERMINING THE REFRACTIVE ERROR OF AN EYE

(71) Applicant: Carl Zeiss Vision International GmbH, Aalen (DE)

(72) Inventors: Nikolai Suchkov, Tübingen (DE); Alexander Leube, Aalen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/450,132

(22) Filed: Aug. 15, 2023

(65) Prior Publication Data

US 2023/0380681 A1    Nov. 30, 2023

Related U.S. Application Data

(63) Continuation of application No. PCT/EP2022/053899, filed on Feb. 17, 2022.

(30) Foreign Application Priority Data

Feb. 17, 2021 (EP) .................................. 21157673

(51) Int. Cl.
*A61B 3/103* (2006.01)
*A61B 3/00* (2006.01)
*A61B 3/14* (2006.01)

(52) U.S. Cl.
CPC ............ *A61B 3/103* (2013.01); *A61B 3/0008* (2013.01); *A61B 3/14* (2013.01)

(58) Field of Classification Search
CPC .......... A61B 3/103; A61B 3/0008; A61B 3/14
USPC .......................................................... 351/206
See application file for complete search history.

(56) References Cited

U.S. PATENT DOCUMENTS

2005/0030477 A1    2/2005 Lai et al.
2006/0007397 A1*   1/2006 Lai ....................... A61B 3/0285
                                                        351/205

(Continued)

FOREIGN PATENT DOCUMENTS

CN    102085089 A    6/2011
CN    104768499 A    7/2015

(Continued)

OTHER PUBLICATIONS

Atchison et al., "Useful Variations of the Badal Optometer," Optom. Vis. Sci., vol. 72, No. 4, pp. 279 to 284, Apr. 1995.

(Continued)

*Primary Examiner* — Mohammed A Hasan
(74) *Attorney, Agent, or Firm* — Tautz & Schuhmacher LLC; Georg M. Hasselmann

(57) ABSTRACT

Apparatuses and methods for determining a refractive error of an eye are disclosed. A series of images of light coming from an eye are captured with varying optical powers, and the refractive error is then calculated based directly on the series of images used as approximate point spread functions. The calculation includes determining a modulation transfer area as a function of meridian angle and optical power in an angle range from 0° to 180° based on the series of images, and to calculate the refractive error based on the modulation transfer area as a function of angle and optical power.

20 Claims, 5 Drawing Sheets

(56) References Cited

U.S. PATENT DOCUMENTS

| | | | |
|---|---|---|---|
| 2008/0147185 A1* | 6/2008 | Hong | A61F 2/1613 623/6.34 |
| 2011/0128498 A1 | 6/2011 | Nakamura | |
| 2015/0250585 A1* | 9/2015 | Rosen | A61F 2/1613 623/6.26 |
| 2015/0277145 A1 | 10/2015 | Bakaraju et al. | |
| 2017/0079523 A1* | 3/2017 | Limon | A61B 3/036 |
| 2019/0246891 A1 | 8/2019 | Ohlendorf et al. | |
| 2020/0237210 A1* | 7/2020 | Limon | G01S 17/88 |

FOREIGN PATENT DOCUMENTS

| | | |
|---|---|---|
| CN | 109996483 A | 7/2019 |
| EP | 2026693 B1 | 7/2019 |
| ES | 482663 A1 | 11/1980 |
| TW | 201521673 A | 6/2015 |
| TW | 201523067 A | 6/2015 |
| WO | 2020249679 A1 | 12/2020 |

OTHER PUBLICATIONS

Thibos et al., "Power Vectors: An Application of Fourier Analysis to the Description and Statistical Analysis of Refractive Error," Optometry and Vision Science, vol. 74, No. 6, pp. 367 to 375, 1997.

Colicchia et al., "Measuring aberration of the eye with wavefront technology," Physics Education, vol. 41, No. 4, pp. 307 to 310, Jul. 2006.

Asatryan et al., "Optical lens with electrically variable focus using an optically hidden dielectric structure," Optics Express, vol. 18, No. 13, pp. 13981 to 13992, Jun. 2010.

Vinas et al., Longitudinal chromatic aberration of the human eye in the visible and near infrared from wavefront sensing, double-pass and psychophysics, Optics Express, vol. 23, No. 4, pp. 948 to 962, Feb. 2015.

Industrial Norm "Ophthalmic optics—Spectacle lenses—Vocabulary (ISO 13666:2012)," German and English version EN ISO 13666:2012, Oct. 2013.

Extended European Search Report issued in EP 21 157 673.1, to which this application claims priority, dated Aug. 10, 2021.

International Search Report and Written Opinion issued in PCT/EP2022/053899, to which this application claims priority, dated May 11, 2022.

International Preliminary Report on Patentability issued in PCT/EP2022/053899, to which this application claims priority, dated Jan. 18, 2023.

Office Action by the Chinese Patent Office issued in CN 2022800153847, which is a counterpart hereof, dated Nov. 29, 2023, and English-language translation thereof.

* cited by examiner

APPARATUS AND METHOD FOR DETERMINING THE REFRACTIVE ERROR OF AN EYE

CROSS REFERENCE TO RELATED APPLICATIONS

This application is a continuation application of international patent application PCT/EP2022/053899, filed on Feb. 17, 2022 and designating the U.S., which claims priority to European patent application EP 21 157 673.1, filed on Feb. 17, 2021, both of which are hereby incorporated by reference in their entireties.

TECHNICAL FIELD

The present application relates to apparatuses and methods for determining the refractive error of an eye as well as to kits and computer programs associated therewith.

BACKGROUND

Determining the refractive error of an eye is an important part of eye examinations, the result of which is for example used to produce lenses for eyeglasses with appropriate optical properties for the respective eye or to prescribe appropriate contact lenses. In the field of ophthalmology, the refractive error of an eye is usually given in terms of sphere, also referred to as spherical power, as defined in 11.2 of DIN EN ISO 13666:2013-10, cylinder, also referred to as cylindrical power, as defined under 12.5 of DIN EN ISO 13666:2013-10 and axis, more precisely cylinder axis, as defined under 12.6 of DIN EN ISO 13666:2013-10. These values give essentially the deviations from an emmetropic eye (zero refractive error). Values of 0 for sphere and cylinder indicate that the eye is emmetropic, while values different from 0 indicate various kinds of ametropia like hyperopia or myopia.

A determination of the refractive error may be a subjective refractive error determination or objective refractive error determination. Methods for subjective refractive error determination are based on a (subjective) feedback of an examined person regarding his or her visual perception. An example is a measurement on the basis of eye charts with small and smaller symbols, letters, numbers or the like, where the person gives feedback which numbers, letters or symbols he or she can recognize. Lenses may then be placed in front of the eye of the person, and the person may give feedback with which lenses the best visual perception is obtained. An example for apparatuses allowing subjective refractive error determinations are phoropters. Methods and apparatuses for objective refractive error determination do not need such a feedback of the examined person regarding his or her visual perception.

Examples of apparatuses for objective refractive error determination are Hartmann-Shack-based aberrometers, as for example described in G. Colicchia and H. Wiesner, Physics Education, Volume 41, No. 4. Such aberrometers are comparatively complex and therefore are costly apparatuses which require a camera and lenslet array for sensing wavefronts. The measurement range of such aberrometers is limited by the parameters of the lenslet array and is inversely proportional to the accuracy, i.e. a higher measurement range typically will result in lower accuracy.

Another class of apparatuses used for objective refractive error determination are referred to as autorefractors are based on principles described in Spanish patent application ES 482663 A1 and are available commercially in many forms, for example as the Zeiss Visuref 100 or 150. Such autorefractors often exhibit a comparatively low accuracy compared to aberrometers, in particular in case of a positive refractive error, i.e. hyperopic subjects. Therefore, the result of such autorefractors is often only used as a starting point to then perform a subjective refractive error determination as a more exact measurement.

SUMMARY

Commercial autorefractors and aberrometers are comparatively costly and have a certain size, which makes them difficult to move around. Therefore, starting from such conventional apparatuses for objective refractive error determination and corresponding methods, it is an object of the present disclosure to provide apparatuses and methods which are capable of remedying at least some of the drawbacks above, in particular providing a possibility for objective refractive error determination with low costs and/or with a compact design.

WO 2020/249 679 A1 discloses an apparatus for determining the refractive error of an eye using a smartphone. An image of a retina of the eye is captured and convolved with point spread functions corresponding to different defocus values. Point spread functions are determined based on images using complex mathematical operations like a neural network or using convolutions and deconvolutions. The refractive error is the determined based on the defocus of the best fitted point spread function.

US 2005/030 477 A1 uses wavefront sensing and laser illumination to determine a refractive error of an eye.

EP 2 026 693 B1 discloses a subjective refraction error determination method.

An apparatus for determining the refractive error of an eye and a method for determining the refractive error of an eye are provided. Further, a corresponding computer program, a kit for a mobile computer device, and a method for producing a lens for spectacle glasses are disclosed.

An apparatus for determining a refractive error of an eye is provided, comprising: a camera configured to capture an image of light from the eye, an optical power changing device configured to vary an optical power of a path from the eye to the camera, and a computing device.

According to a first aspect, the apparatus is characterized in that the computing device is configured to calculate the refractive error based on a series of images of light from the eye captured by the camera with varying optical power using the series of images directly as at least approximate point spread functions. The point spread function of the optical path from the eye to the camera is an intensity distribution resulting from the eye being illuminated at a single spot. As will be explained further below, in some exemplary embodiments no point illumination device, but a more extended illumination device may be used, in which case the intensity distributions of the images represent approximate point spread function.

According to a second aspect, the apparatus is characterized in that the computing device is configured to calculate the refractive error based on a series of images of light from the eye captured by the camera with varying optical power using the series of images as at least approximate point spread functions. In this second aspect, to calculate the refractive error, for at least three different meridians corresponding to three different directions in the images captured, an optical power setting where the point spread function is sharpest (narrowest) may be determined. This is equivalent to determining the maximum of an area (integral) of the modulation transfer function (MTF) for the three meridians.

In this way, in contrast to for example autorefractors which require several series of images with different illuminations for different meridians, the apparatus may calculate the refractive error, for example in terms of sphere, cylinder and axis, based on a single measurement series with varying optical power. As any measurement, the measurement may be repeated to increase accuracy, but a single measurement is sufficient.

In addition, in contrast to WO 2020/249 679 A1, the series of images of light from the eye captured is used as a point spread function, so no image of the retina needs to be captured. The term "directly" emphasizes this, i.e. point spread functions are not calculated based on retinal images using convolutions or neural networks, but the images themselves are used as at least approximate point spread functions. The term "image of light from the eye" indicates this, i.e. the images do not have the purpose of capturing structures of the eye itself, but have the purpose of capturing a light intensity distribution of light coming from the eye, e.g. in response to illumination with a light source internal or external to the apparatus as explained further below.

The optical power of the light path determines the focus with which the light from the eye is imaged to the camera and/or the size with which the light from the eye appears in the image. In some exemplary embodiments, the optical power changing device may include a variable focus optic. A variable focus optic generally is an optical device the focal length of which may varied. Such a variable focus optic may for example comprise one or more lenses, a focal length of which may be varied. Such lenses may for example include a lens with electrically variable focus as discussed in K. Asatryan et al., Optics Express, Volume 18, No. 13, liquid lenses, or an optic with two or more lenses, some of which are movable with respect to other lenses. Other examples include lens- or minor-based Badal systems (D. A. Atchison, A. Bradley, L. N. Thibos, and G. Smith, "Useful Variations of the Badal Optometer," Optom. Vis. Sci. 72, 279-284 (1995)), deformable mirrors, spatial light modulators (SLMs) or a set of polarization-dependent lenses.

Another example for an optical power changing device causes axial movement of fixed focal length lenses within the system, or of the detector device. A range through which the optical power of the optical power changing device can be varied corresponds to a measurement range of the apparatus. By providing on optical power changing device with a wide range of optical power settings, a correspondingly large measurement range may be easily obtained. In other exemplary embodiments, the optical power setting device may be implemented in software on the computing device to computationally vary the optical power.

For determining the refractive error of an eye, the computing device may control the optical power changing device to vary the optical power, while the controlling the camera to capture images of light from the eye for each optical power setting to obtain the series of images.

In some implementations, the computing device is a mobile computer device like a smartphone and a tablet computer, and the camera may be a camera of the smartphone or tablet computer. In this way, the apparatus may be implemented at comparatively low costs by using an existing smartphone or tablet computer. Furthermore, the optical power changing device may be an autofocus device of the camera, for example camera of the mobile computer device. This may further decrease implementation costs. However, also in case of using a mobile computer device like a smartphone, a separate optical power changing device may be provided to increase a measurement range compared to an autofocus. In yet other exemplary embodiments, the optical power changing device may be implemented in software on the computing device to computationally change the optical power. A computational implementation of an optical power changing device may for example be implemented similar to the above mentioned WO 2020/249679 A1, with the difference that no retinal image is convolved with point spread functions representing different optical power (defocus values), but the image used as an at least approximate point spread function is convolved with point spread functions representing different optical powers.

The apparatus may further include an illumination device for creating a focal spot on the retina of the eye for the measurement, which, when back-propagated, produces point spread functions (of the point corresponding to the focal spot) for the varying optical powers on the camera. In case a non-point illumination device like a light emitting diode, LED, is used, the detector device measures essentially a superposition of all point spread functions of points of the light on the eye. This, may be seen as an approximation of the point spread function and may also be used for measurements as described herein. Therefore, a point illumination device like a focused laser is not required, but may be used for more precise measurements. Typically, the illumination device uses infrared light, in particular an infrared laser. In this way, the person examined does not notice the light used for the measurement. Such an illumination device may be placed at various parts of the apparatus, and light may be guided to the eye using elements like mirrors, including for example a semitransparent mirror, and/or lenses.

However, due to chromatic aberration of the eye, the values of sphere, cylinder and axis thus calculated using infrared light differ from the values for visible light, for which lenses ultimately have to be designed. Therefore, a correction of this deviation due to chromatic aberration of the optical power of the eye as a function of wavelength may be performed in some exemplary embodiments, for which previously reported values of longitudinal chromatic aberrations may be used, such as in M. Vinas, C. Dorronsoro, D. Cortes, D. Pascual, and S. Marcos, "Longitudinal chromatic aberration of the human eye in the visible and near infrared from wavefront sensing, double-pass and psychophysics," Biomed. Opt. Express 23, 513-522 (2015).

In other exemplary embodiments, an illumination device external to the apparatus may be used, which may be a point illumination device like a laser or an approximation of a point source like a light-emitting diode. For example, a beam diameter of the illumination device may be below 2 mm, for example below 1.5 mm, typically below 1 mm.

In the following, for simplicity's sake, reference will be made only to the point spread function, understanding that depending on the illumination used this may also be an approximate point spread function.

Several approaches may be made for determining the refractive error in terms of sphere, axis and cylinder. In a first approach, which is implemented in the second aspect above, but which may also be used for the first aspect, for at least three different meridians corresponding to three different directions in the images captured, an optical power setting where the point spread function is sharpest (narrowest) may be determined. This is equivalent to determining the maximum of an area (integral) of the modulation transfer function (MTF) for the three meridians. The modulation transfer function essentially corresponds to the absolute value of the optical transfer function (OTF), which is defined as the Fourier transfer of form of the point spread function For example, for the three meridians, 0°, 45° and 90°, which may correspond to a horizontal direction, 45° direction and vertical direction in the images captured, may be used. With these angular values, the calculation is particularly simple, but other angular values may be used as well. Details regarding such calculations may be found in L. N. Thibos, W. Wheeler, and D. Homer, "Power vectors: an application of Fourier analysis to the description and statistical analysis of refractive error," Optom. Vis. Sci. 75, 367-375 (1997).

With $P_0$, $P_{45}$, and $P_{90}$ being the respective optical power settings in Diopters (D) of the optical power provided by the optical power changing device or computationally varied optical power in the pupil plane of the eye in terms of a deviation from a 0 setting for three meridians of 0°, 45° and 90°, respectively, where the point spread function is sharpest (or the MTF area is at its maximum), a value M can be calculated according to $$M=(P_0+P_{90})/2,$$

and power vectors $J_0$, $J_{45}$ can be calculated according to $$J_0=P_0-M$$

$$J_{45}=P_{45}-M$$

From that, the cylinder J may be calculated according to $$J=\sqrt{J_0^2+J_{45}^2},$$

and the axis α may be calculated according to $$\alpha = \frac{1}{2}\tan^{-1}(J_{45}/J_0).$$

The sphere corresponds to M.

Thus, sphere, cylinder and axis may be calculated.

The typical optometric notation of negative cylinder can be calculated as follows:

$$S'=M+J$$

$$C'=-2J$$

As briefly mentioned above, in case an infrared illumination device is used, the above values have to be corrected taking the chromatic aberration of the human eye into account. For instance, chromatic shift from 555 nm to 780 nm would be around 0.8 D. Then, for calculating the refraction values, 0.8 D should be subtracted from M, $P_0$, and $P_{45}$ as used in the equations above.

In a second approach to determining sphere, axis and cylinder, the maximum area of the modulation transfer function depending on optical power setting is calculated for a plurality of meridians over at least 180° with a step size smaller than 20°, typically smaller than 10°, more typically 5° or smaller, for example 1°. Then, the refractive error is calculated based on the area of the modulation transfer function as a function of optical power setting and angle.

For example, in case of the eye having no cylinder (i.e. no spherical aberration), the optical power setting is setting at which the modulation transfer area has its maximum corresponds to the sphere. In case of an astigmatism (cylinder≠0), there are two maximums in the modulation transfer function area depending on angle and optical power setting. The sphere is then the optical power setting value of one of the maximums, the cylinder is the difference of optical power settings between the maximums, and the axis is the angle difference between the two maximums. The number of maximums and their angular position may be calculated first by averaging the modulation transfer function are over 180°.

This evaluation may for example be performed by image analysis efficiently.

A corresponding method is also provided, which includes capturing a series of images of an eye with varying optical power, and calculating the refractive error based on the series of images, as explained above for the first and second aspect. The method may further include illuminating the eye with an illumination device as discussed above. The above explanations made for the apparatus also apply to the method, for example the different ways of calculating the refractive error based on the images.

The method may be implemented in form of a computer program, for example in form of an application (app) for a mobile computer device like a smartphone or a tablet. The computer program may be provided on a tangible storage medium. In other words, the computer program may, when executed on a computing device, cause the computing device to cause execution of the method as discussed above, for example by controlling an apparatus as discussed above and performing calculations for refractive error determination.

In this case, the computer program may be included in a kit for a mobile computer device, where the kit, in addition to the computer program, may include a hardware module to be connected to the smart phone. The hardware module may include one or more hardware elements from the group consisting of an illumination device as mentioned above and an optical power changing device as mentioned above, and may also include further optical elements like lenses or mirrors. With such a kit, a conventional mobile computer device like a smartphone may be converted to an apparatus as mentioned above.

The refractive error determined by the above apparatuses, methods, computer programs and kits, may then be used for producing lenses based on the refractive error, i.e. lenses to correctly refractive error of the eye.

BRIEF DESCRIPTION OF THE DRAWINGS

The disclosure will now be described with reference to the drawings wherein.

DESCRIPTION OF EXEMPLARY EMBODIMENTS

Figure 1:
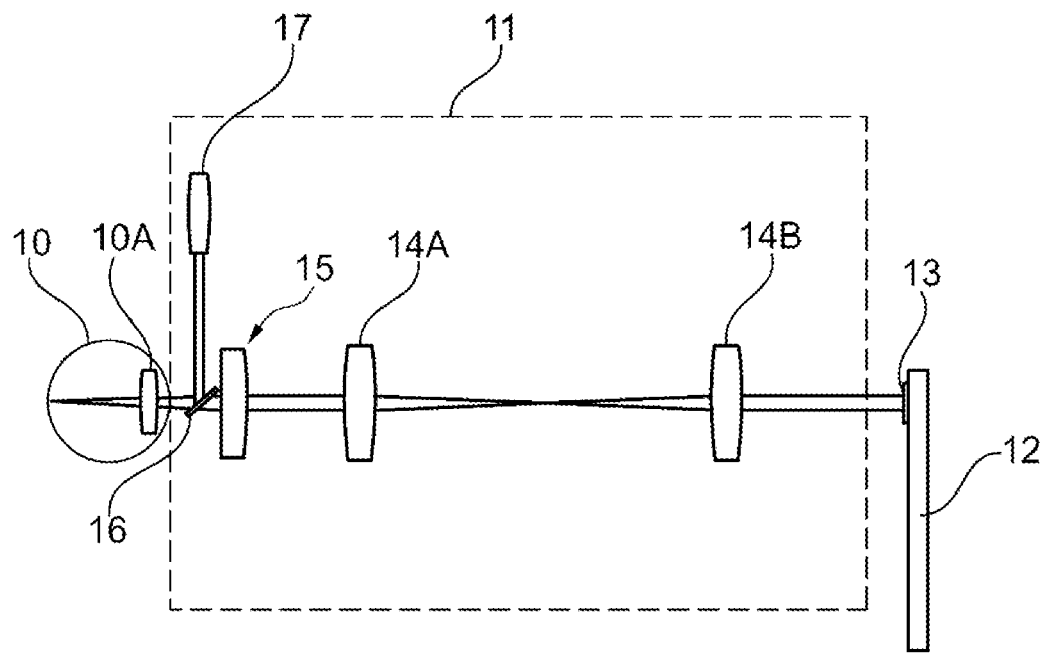
FIG. 1 is an apparatus for determining the refractive error of an eye according to an exemplary embodiment.

FIG. 1 is a diagram illustrating an apparatus for determining a refractive error of an eye 10 having optical properties represented by a lens 10A according to an exemplary embodiment.

It should be noted that while single lenses are depicted in several instances in the exemplary embodiment of FIG. 1, these may be replaced by combinations of two or more lenses or by other optical elements like diffractive elements having the same or similar optical function.

The apparatus of FIG. 1 includes a mobile computer device 12, in the example of FIG. 1 a smartphone, and a hardware unit 11 coupled to computer device 12. In other exemplary embodiments, instead of a smartphone other mobile computer devices like a tablet PC, or a laptop computer may be used.

Hardware unit 11 may be coupled to mobile computer device 12 using for example adhesive, brackets or other fastening elements, which align hardware unit 11 to a camera 13 of mobile computer device 12.

In other exemplary embodiments, instead of using a pre-existing mobile computer device 12 like a smartphone, a dedicated apparatus may be provided including for example elements of hardware unit 11, a camera corresponding to camera 13 and a computing device having processing capabilities using processors, memories and the like, which in case of FIG. 1 is performed by mobile computer device 12.

Hardware unit 11 includes an infrared laser 17 as an illumination device. Light from infrared laser 17 is reflected by a semitransparent mirror 16 through lens 10A into eye 10.

By using an infrared laser, or infrared light in general, the person examined (i.e. the person to whom eye 10 belongs) does not notice the examination due to light coming into the eye. Infrared laser 17 may be regarded as approximately being a point illumination device. As mentioned above, also other illumination devices, for example light-emitting diodes, may be used.

Light reflected from the retina of eye 10 through lens 10A passes through semitransparent mirror 16, a variable focus optic 15 symbolized by a focus-adjustable lens in FIG. 1 and an optics arrangement including lenses 14A and 14B. Variable focus optic 15 is a simple example for an optical power changing device and may be implemented as explained above, for example using an adjustable liquid lens or any of the other possibilities mentioned above, including an arrangement of several lenses or other optical elements as well as moving lenses or moving a camera 13. The placement of variable focus optic 13 is also only an example, and other placements may be used, for example a placement between lens 14B and camera 13, or a placement between lenses 14A and 14B.

Lenses 14A, 14B form a telescope arrangement imaging light from eye 10 on camera 13.

A setting of variable focus optic 15 will also be referred to as defocus in the following. For an emmetropic eye (no astigmatism, sphere=0), a defocus of 0 means that the retina of eye 10 is imaged sharply on camera 13.

In other exemplary embodiments, variable focus optic 15 may be omitted, and an autofocus of camera 13 may be controlled to perform the function of an optical power changing device, as explained above and further below. However, by using a separate variable focus optic, a measurement range (a range from maximum negative defocus to maximum positive defocus) may be extended. In yet other exemplary embodiments, as explained above, other optical power changing devices that a variable focus optic may be used.

Figure 2:
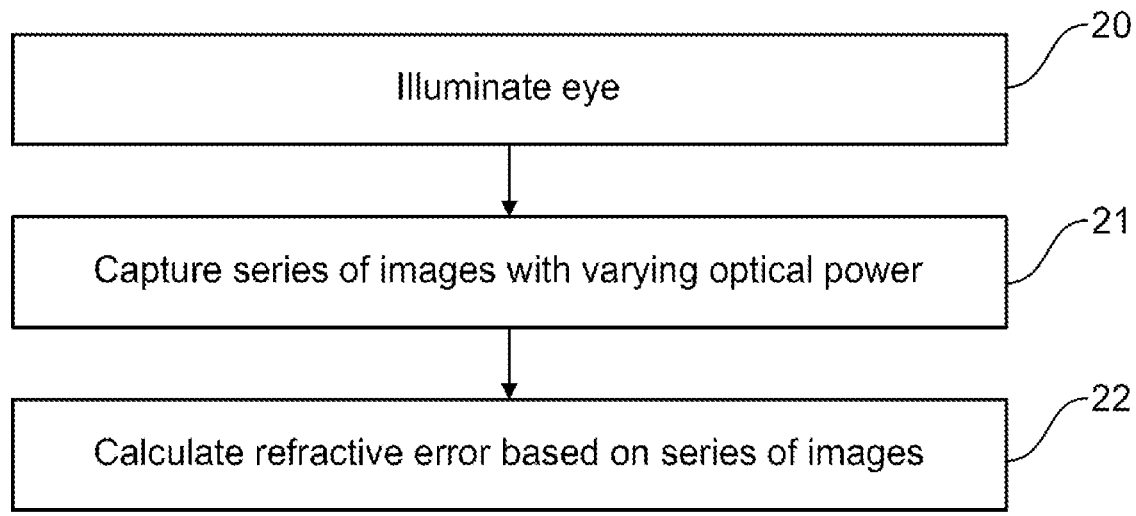
FIG. 2 is a flowchart illustrating a method according to an exemplary embodiment.

FIG. 2 is a flowchart illustrating a method according to an exemplary embodiment. The method of FIG. 2 is an example for operation of the apparatus of FIG. 1 and will be explained referring to FIG. 1.

In step 20, the method includes illuminating an eye. In case of FIG. 1, this illumination is performed by infrared laser 17 via semitransparent mirror 16.

In step 21, the method comprises capturing a series of images with varying optical power. In the exemplary embodiment of FIG. 1, computing device 12 controls variable focus lens 15 to provide different defocus settings, corresponding to varying optical power, and controls camera 13 to capture an image for each defocus setting, thus resulting in a series of images. In step 22, the method comprises calculating the refractive error, for example in terms of sphere, cylinder and axis, based on the series of images. Each image essentially corresponds to the point spread function or at least approximate point spread function for the respective defocus setting, and the refractive error is calculated essentially based on the point spread functions.

Different possibilities for calculating the refractive error will now be explained using examples referring to FIGS. 3 to 6.

Figure 3A:
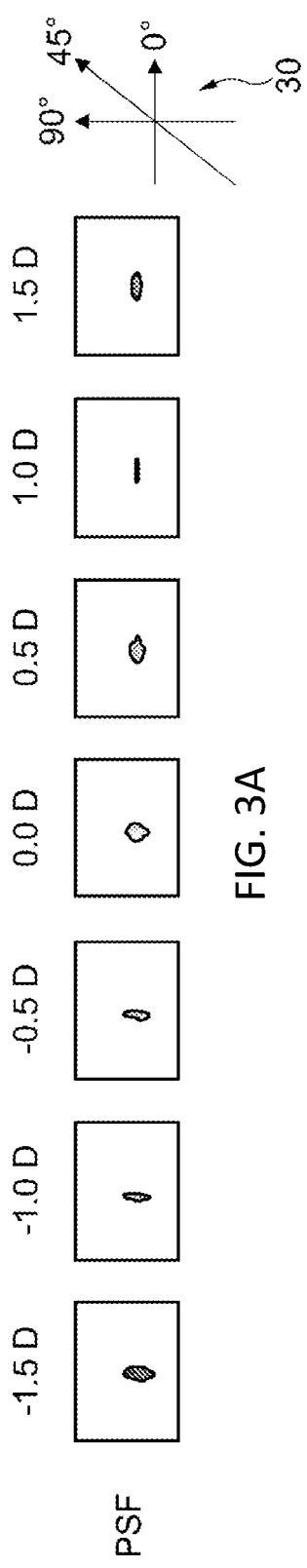
FIG. 3A shows example images as measurement results for illustrating some exemplary embodiments.

FIG. 3A shows example images representing the point spread function captured with camera 13 of FIG. 1 for defocus settings from −1.5 diopters (D) to 1.5 D in steps of 0.5 D. Of course, the step size of 0.5 D is only an example, and to increase accuracy also a smaller step size, for example 0.1 D, may be used. The intensity in the image (e.g. greyscale value, mean RGB value) correspond to the amplitude of the point spread function.

Figure 3B:
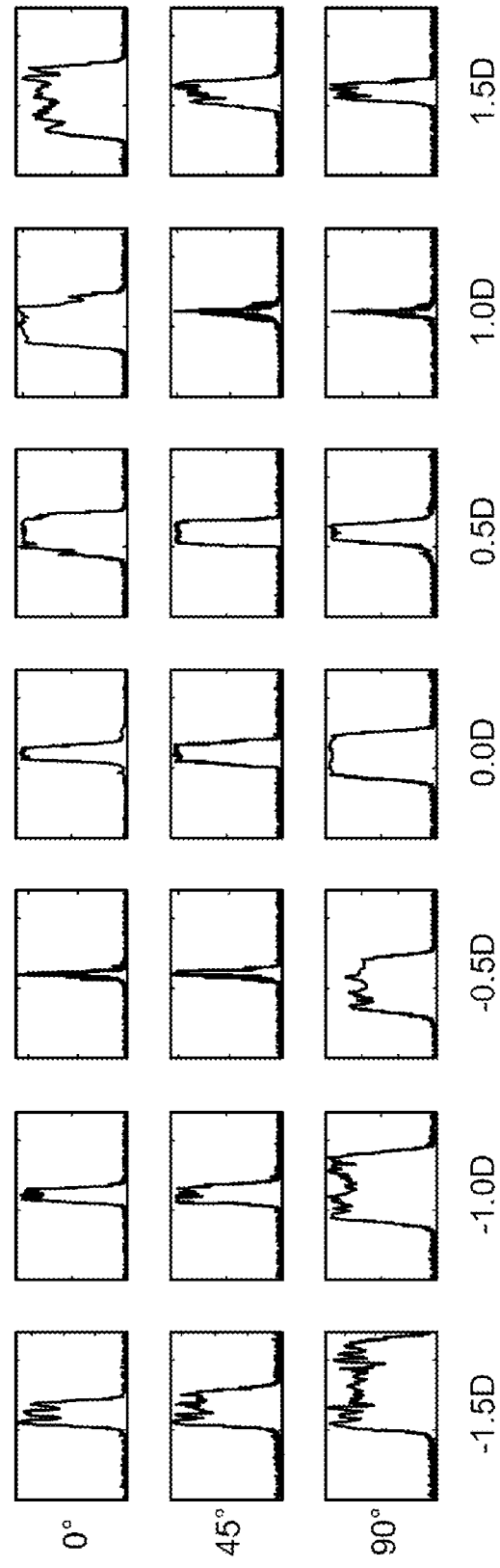
FIG. 3B shows intensity distributions of the images of FIG. 3A for different angles.

In a first evaluation approach, the "best focus", i.e. a defocus setting where the point spread function is sharpest, is determined for three different meridians, i.e. three different directions in the images of FIG. 3A. In an example discussed herein below, meridians of 0°, 45° and 90° are used, where the directions are shown at 30 in FIG. 3A. In other exemplary embodiments, other angles may be used, with corresponding modifications to the calculations set forth below, in some exemplary embodiments, the best focus may be found by evaluating the images directly, i.e. by evaluating the shape of point spread function curves in three directions. To illustrate this, FIG. 3B illustrates intensities for the images of FIG. 3A along lines having a 0° angle (top row), 45° angle (middle row) and 90° (bottom row). As can be seen, for different meridians the peaks are sharpest at different defocus settings, for example at −0.5D for 0° or at 1.0D for 45° and 90°.

In other exemplary embodiments, the modulation transfer function (MTF) may be calculated for the three meridians, and an area (integral) of the modulation transfer function may be determined.

Figure 4:
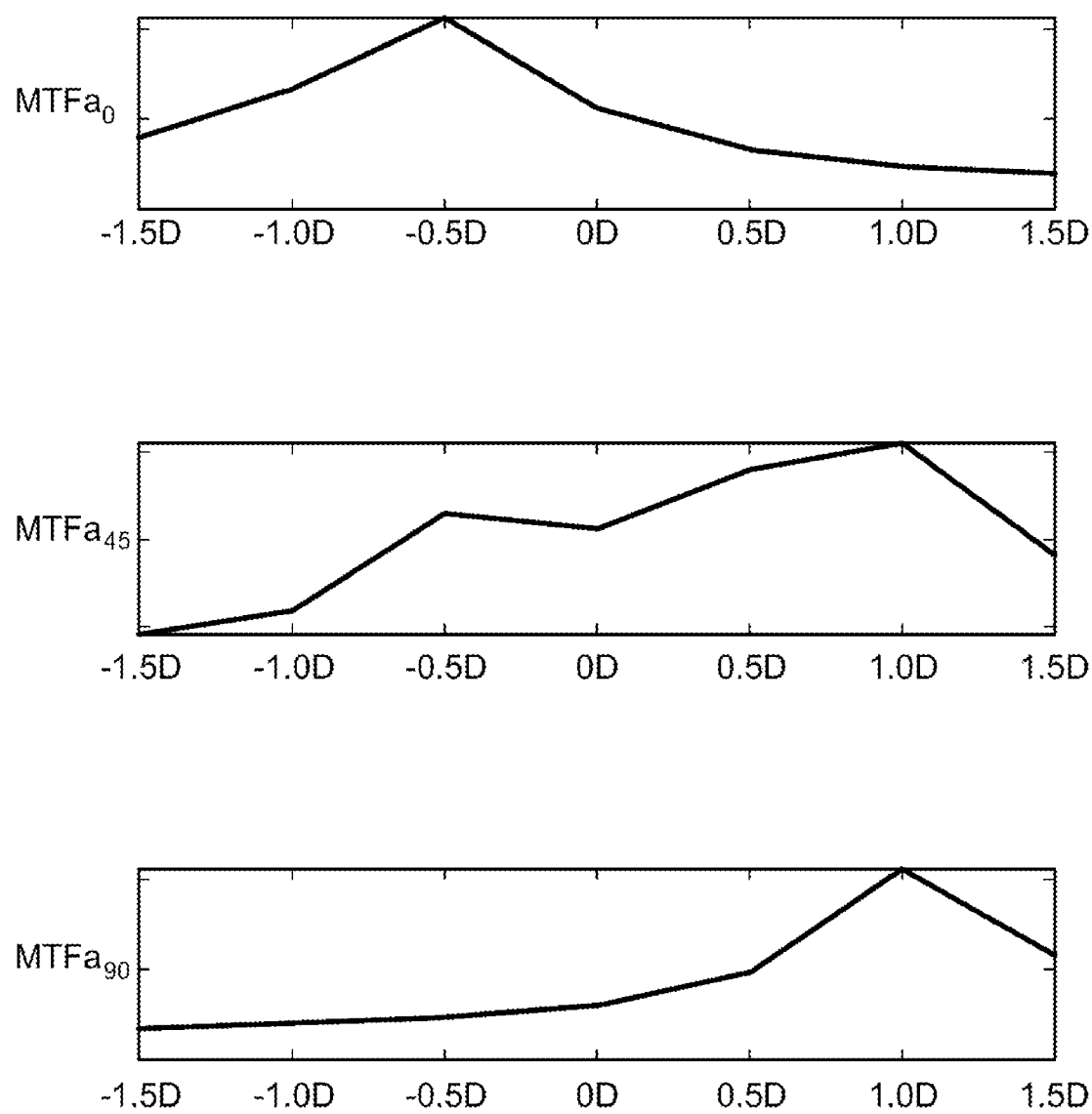
FIG. 4 illustrates modulation transfer function areas calculated based on the measurement results of FIG. 3B.

An example for the images of FIG. 3A is shown in FIG. 4, where the modulation transfer function area (MTFa) is shown over the defocus for the three meridians of 0° (MTFa$_0$), 45° (MTFa$_{45}$) and 90° (MTFa$_{90}$). The best focus then corresponds to the respective maximum of the area. In the example shown, for 0° the maximum is at −1.0 D, for 45° the maximum is at 0.5 D, and for 90° the maximum is at 1.0 D.

Furthermore, the measurement may be repeated, to increase accuracy through a plurality of measurements by statistics, as essentially possible for all measurements. For such multiple measurements, also the angle may be varied slightly. For example, for finding the best focus for 45°, meridians in a range around 45°, for example from 43° to 47°, may be evaluated, and the average best focus settings then may be used as for all these angles then may be used as the best focus setting for 45°. This was done for the MTFa functions shown in FIG. 4.

With $P_0$ being the defocus value of the best focus setting for 0°, $P_{45}$ being the best focus setting for 45° and $P_{90}$ being the best focus setting for 90°, sphere, cylinder and axis may then be calculated according to the following equations. In the example of FIGS. 3A, 3B, and 4, $P_0$ would be −1.0 D, $P_{45}$ would be 0.5 D, and $P_{90}$ would be 1.0 D. Of course, these values are very depending on the eye being examined.

In particular, sphere M may be calculated as $$M = (P_0 + P_{90})/2.$$

Cylinder J and axis α may be calculated according to $$J_0 = P_0 - M$$

$$J_{45} = P_{45} - M$$

$$J = \sqrt{J_0^2 + J_{45'}^2},$$

and $$\alpha = \frac{1}{2}\tan^{-1}(J_{45}/J_0).$$

These values may then be corrected to compensate chromatic aberration as discussed above.

For instance, chromatic shift from 555 nm to 780 nm would be around 0.8 D. Then, for calculating the refraction values, 0.8 D should be subtracted from M, $P_0$, and $P_{45}$ as used in the equations above.

An alternative evaluation method of the image captured will be explained referring to FIG. 5 (including subfigures 5A and 5B) and 6 (including subfigures 6A and 6B). In the alternative approach, as explained for FIG. 4, the modulation transfer area MTFa is calculated for each optical power setting, for example defocus settings as shown in FIG. 3B. However, in contrast to the example of FIG. 4, the modulation transfer focus area is not calculated only for three meridians, that over 180° in a certain step size, for example 10°, 5° or 1°, even if other step sizes or varying step sizes may also be used. Generally, using a smaller step size increases the accuracy, but also increases the computation time required. In this way, the modulation transfer area MTFa is determined as a function of defocus setting and angle.

Figure 5A:
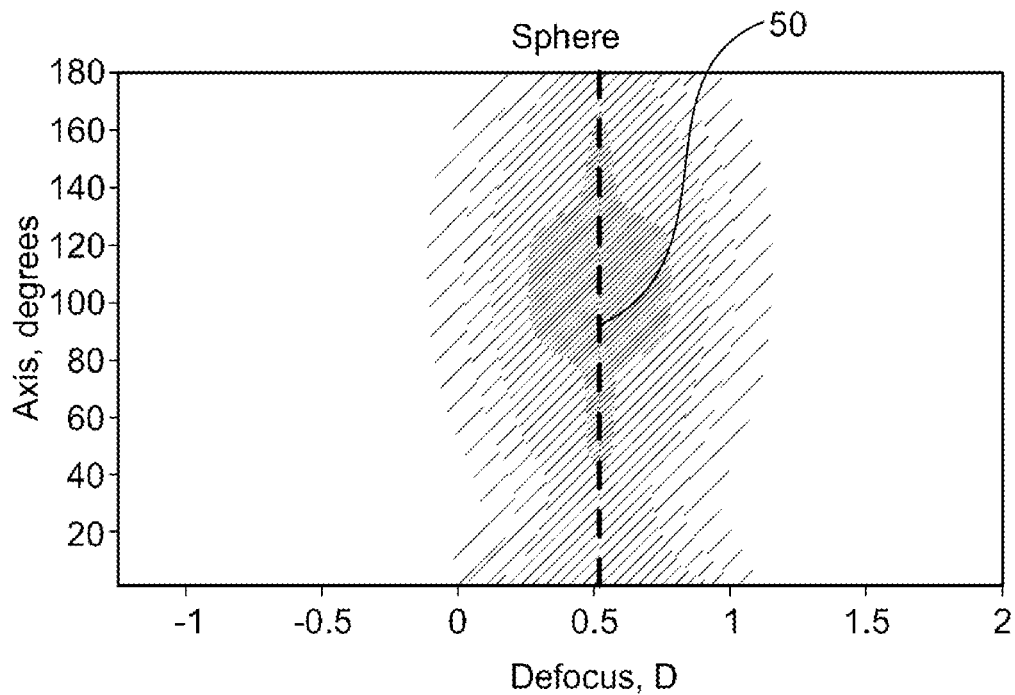
FIGS. 5A and 5B illustrates an evaluation of measurements for an eye having only spherical aberration.
Figure 5B:
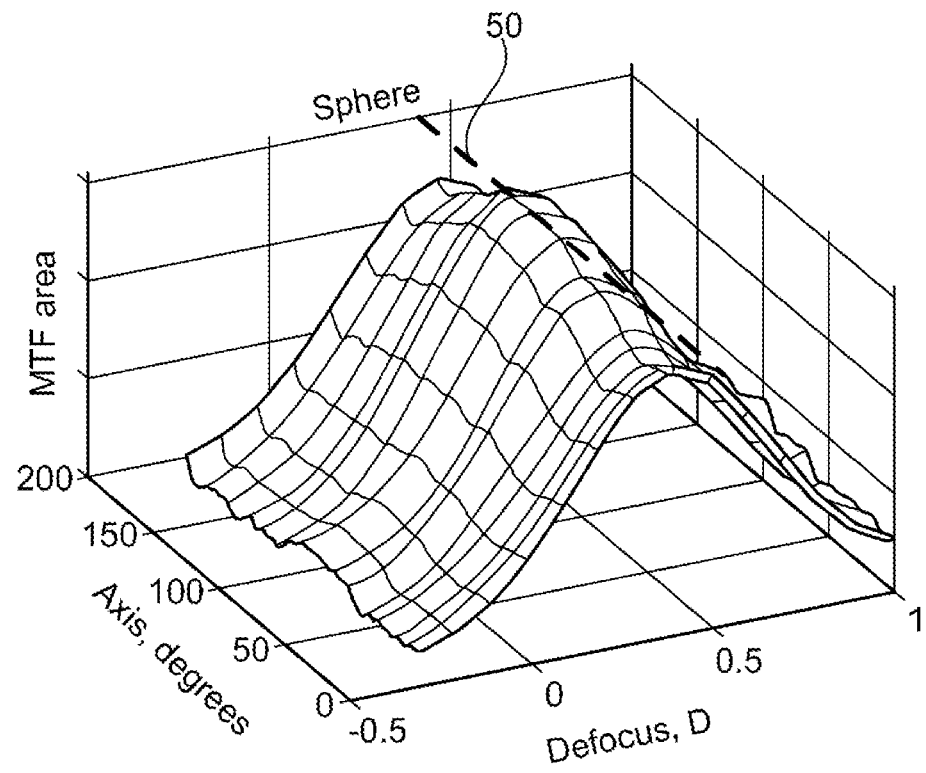
Figure 6A:
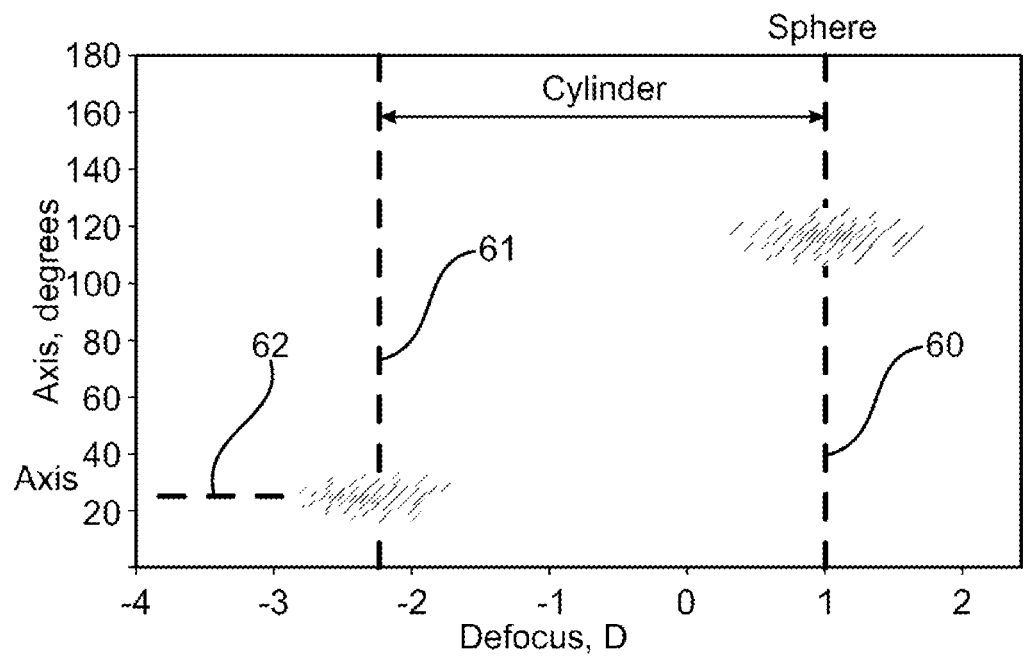
FIGS. 6A and 6B shows an example evaluation of measurements for an eye having astigmatism.
Figure 6B:
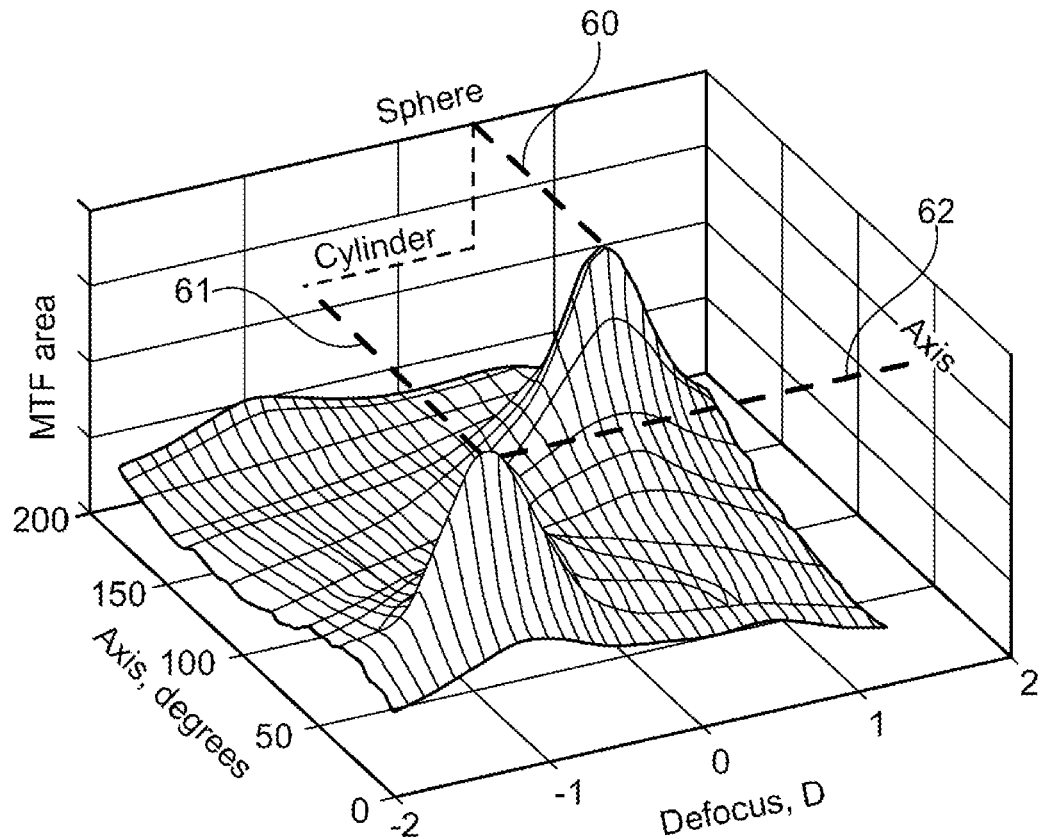

This function may be represented as an image, where the modulation transfer function area corresponds to the intensity (e.g. greyscale value, brightness value or the like) and the x- and y-coordinates in the image represent defocus setting and angle or as a 3D Plot. FIGS. 5 and 6 show corresponding examples for two sets of measurements, where in FIG. 5 no astigmatism is present in the eye (cylinder=0), whereas in FIG. 6 an astigmatism is present. In FIGS. 5A and 6A, an image representation is given, whereas in FIGS. 5B and 6B, a representation as a 3D Plot is used. In FIGS. 5A and 6A, a more dense hatching represents a higher intensity. In FIGS. 5 and 6, the defocus is on the x-axis, the angle of the Meridian measured is on the y-axis, and the intensity of the image represents the area of the modulation transfer function.

The values of sphere, cylinder and axis may then be found using simple image processing. In case of no astigmatism present (FIG. 5), independent of the direction, the maximum area is always at the same defocus, indicated by a line 50 in FIG. 5. In the example of FIG. 5, for example the sphere value would be 0.5. This value may for example also be found by calculating a mean area across all meridians (angles). In case of a significant value of astigmatism, for example more than 0.25 D, two peaks will be found in the mean modulation transfer function overall angles depending on the focus. This corresponds to two peaks found in FIG. 6. The sphere value then is at the defocus value corresponding to the peak at a higher defocus, in case of FIG. 6 at 1 D, as indicated by a line 60. The cylinder value corresponds to the difference in defocus between the two peaks, i.e. the difference on the defocus, x, axis between line 60 and 61 of FIG. 6. The axis value corresponds to the position of the second peak (with lower defocus) on the y, angle, axis as indicated by a line 62. In this way, by evaluating the modulation transfer area as a function of angle and defocus, sphere, cylinder and axis may be found.

The thus determined refractive error may then be used for producing a lens for spectacle glasses based on the refractive error to correct the refractive error. To this end, the determined refractive error may be transmitted to a lens manufacturer, for example by using an Internet connection established by mobile computer device 13 of FIG. 1.

Some exemplary embodiments are defined by the following examples:

Example 1. An apparatus for determining a refractive error of an eye (10), comprising:
a camera (13) configured to capture an image of light from the eye,
an optical power changing device (15) configured to vary an optical power of a light path from the eye (10) to the camera (13) through a measurement range, and
characterized in that the apparatus comprises a computing device configured to calculate the refractive error of the eye (10) based on a series of images of light from the eye (10) captured by the camera (13) with varying optical power using the series of images as at least approximate point spread functions.

Example 2. The apparatus of example 1, characterized in that the computing device is a mobile computer device including the camera (13).

Example 3. The apparatus of example 1 or 2, characterized in that the optical power changing device includes an autofocus device of the camera (13).

Example 4. The apparatus of example 1 or 2, characterized in that the optical power changing device is implemented as software on the computing device (12) to computationally vary the optical power.

Example 5. The apparatus of any one of examples 1 to 4, characterized by further comprising an illumination device (17) for illuminating the eye (10).

Example 6. The apparatus of example 5, characterized in that the illumination device comprises a point illumination device having a beam diameter of less that 2 mm.

Example 7. The apparatus of any one of examples 1 to 6, characterized in that the computing device is configured to calculate the refractive error by determining an optical power where the point spread function is sharpest for at least three meridians, and calculate the refractive error based on the optical powers where the point spread function is sharpest determined for the at least three meridians.

Example 8. The apparatus according to example 7, characterized in that, for determining the optical powers where the point spread function is sharpest, the computing device is configured to calculate modulation transfer function areas for each of the at least three meridians, and determining the optical power where the point spread function is sharpest as an optical power at a maximum modulation transfer function area for the respective meridian.

Example 9. The apparatus of any one of examples 1 to 6, characterized in that the computing device, for calculating the refractive error, is configured to determine a modulation transfer area as a function of meridian angle and optical power in an angle range from 0° to 180° based on the series of images, and to calculate the refractive error based on the modulation transfer area as a function of angle and optical power.

Example 10. The apparatus of any one of examples 1 to 9, characterized in that the computing device (12) is configured to control the optical power changing device (15) and the camera (13) to capture the series of images of light from the eye.

Example 11. A method for determining a refractive error of an eye (10), comprising:

capturing a series of images of light from the eye (10) with varying optical power in a light path from the eye (10) to a camera (13) used for capturing the series of images, characterized by calculating the refractive error of the eye (10) based on the series of images using the series of images as at least approximate point spread functions.

Example 12. The method of example 11, characterized in that calculating the refractive error comprises determining an optical power where the point spread function is sharpest for at least three meridians, and calculate the refractive error based on the optical powers where the point spread function is sharpest determined for the at least three meridians.

Example 13. The method of example 12, characterized in that determining the optical powers where the point spread function is sharpest comprises calculating modulation transfer function areas for each of the at least three meridians, and determining the optical power where the point spread function is sharpest as an optical power at a maximum modulation transfer function area for the respective meridian.

Example 14. The method of example 11, characterized in that calculating the refractive error comprises determining a modulation transfer area as a function of meridian angle and optical power in an angle range from 0° to 180° based on the series of images, and calculating the refractive error based on the modulation transfer area as a function of angle and optical power.

Example 15. The method of any one of examples 11 to 14, characterized by comprising varying the optical power by at least one action selected from the group consisting of:

varying an autofocus of the camera (13),
controlling an optical power changing device (15), and
computationally varying the optical power.

Example 16. The method of any one of examples 11 to 15, characterized by further comprising illuminating the eye with a beam diameter of less than 2.

Example 17. A computer program, characterized in that the computer program, when executed on a computing device (12), causes execution of the method of any one of examples 11 to 16.

Example 18. A kit, characterized by comprising the computer program of example 17 and a hardware unit (11), the hardware unit (11) comprising at least one element of the group consisting of:

an illumination device (17) for illuminating the eye (10), or
an optical power changing device (15) configured to vary the optical power of the light path from the eye (10) to the camera (13).

Example 19. A method for producing a lens for spectacle glasses, characterized by comprising:

determining the refractive error of an eye according to the method of any one of examples 11 to 16, and producing the lens based on the determined refractive error.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term comprising (and its grammatical variations) as used herein is used in the inclusive sense of having or including and not in the exclusive sense of consisting only of. The terms a and the as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. An apparatus for determining a refractive error of an eye, the apparatus comprising:

a camera configured to capture an image of light from the eye; and
an optical power changing device configured to vary an optical power of a light path from the eye to the camera,
wherein the apparatus includes a computing device which is configured to calculate the refractive error of the eye based on a series of images of light from the eye captured by the camera with varying optical power using the series of images directly as at least approximate point spread functions,
wherein the point spread function is an intensity distribution resulting from the eye being illuminated in a single spot, and
wherein the computing device, for calculating the refractive error, is configured to determine a modulation transfer area as a function of meridian angle and optical power in an angle range from 0° to 180° based on the series of images, and to calculate the refractive error based on the modulation transfer area as a function of angle and optical power.

2. The apparatus of claim 1, wherein the computing device is a mobile computer device including the camera.

3. The apparatus of claim 1, wherein the optical power changing device includes an autofocus device of the camera.

4. The apparatus of claim 1, wherein the optical power changing device is implemented as software on the computing device to computationally vary the optical power.

5. The apparatus of claim 1, further comprising:

a point illumination device having a beam diameter of less that for illuminating the eye.

6. An apparatus for determining a refractive error of an eye, the apparatus comprising:

a camera configured to capture an image of light from the eye; and
an optical power changing device configured to vary an optical power of a light path from the eye to the camera,
wherein the apparatus includes a computing device which is configured to calculate the refractive error of the eye based on a series of images of light from the eye captured by the camera with varying optical power using the series of images as at least approximate point spread functions, by determining an optical power where the point spread function is sharpest for at least three meridians, and calculate the refractive error based on the optical powers where the point spread function is sharpest determined for the at least three meridians.

7. The apparatus of claim 6, wherein the computing device is a mobile computer device including the camera.

8. The apparatus of claim 6, wherein the optical power changing device includes an autofocus device of the camera.

9. The apparatus of claim 6, wherein the optical power changing device is implemented as software on the computing device to computationally vary the optical power.

10. The apparatus of claim 6 further comprising:
a point illumination device having a beam diameter of less that for illuminating the eye.

11. An apparatus for determining a refractive error of an eye, the apparatus comprising:
a camera configured to capture an image of light from the eye; and
an optical power changing device configured to vary an optical power of a light path from the eye to the camera,
wherein the apparatus includes a computing device which is configured to calculate the refractive error of the eye based on a series of images of light from the eye captured by the camera with varying optical power using the series of images as at least approximate point spread functions, by determining an optical power where the point spread function is sharpest for at least three meridians, and calculate the refractive error based on the optical powers where the point spread function is sharpest determined for the at least three meridians, and
wherein, for determining the optical powers where the point spread function is sharpest, the computing device is configured to calculate modulation transfer function areas for each of the at least three meridians, and to determine the optical power where the point spread function is sharpest as an optical power at a maximum modulation transfer function area for the respective meridian.

12. A method for determining a refractive error of an eye, the method comprising:
capturing a series of images of light from the eye with varying optical power in a light path from the eye to a camera used for capturing the series of images; and
calculating the refractive error of the eye based on the series of images using the series of images directly as at least approximate point spread functions,
wherein the point spread function is an intensity distribution resulting from the eye being illuminated in a single spot, and
wherein calculating the refractive error includes determining a modulation transfer area as a function of meridian angle and optical power in an angle range from 0° to 180° based on the series of images, and calculating the refractive error based on the modulation transfer area as a function of angle and optical power.

13. A computer program stored on a non-transitory storage medium, wherein the computer program, when executed on a computing device, causes execution of the method of claim 12.

14. A method for producing a lens for spectacle glasses, the method comprising:
determining the refractive error of an eye according to the method of claim 12; and
producing the lens based on the determined refractive error.

15. A kit comprising:
a computer program stored on a non-transitory storage medium, wherein the computer program, when executed on a computing device, causes execution of a method for determining a refractive error of an eye, the method comprising:
capturing a series of images of light from the eye with varying optical power in a light path from the eye to a camera used for capturing the series of images; and
calculating the refractive error of the eye based on the series of images using the series of images directly as at least approximate point spread functions,
wherein the point spread function is an intensity distribution resulting from the eye being illuminated in a single spot, and
wherein calculating the refractive error includes determining a modulation transfer area as a function of meridian angle and optical power in an angle range from 0° to 180° based on the series of images, and calculating the refractive error based on the modulation transfer area as a function of angle and optical power; and
a hardware unit, the hardware unit including at least one element of the group consisting of:
an illumination device for illuminating the eye and
an optical power changing device configured to vary the optical power of the light path from the eye to the camera.

16. A method for determining a refractive error of an eye, the method comprising:
capturing a series of images of light from the eye with varying optical power in a light path from the eye to a camera used for capturing the series of images; and
calculating the refractive error of the eye based on the series of images using the series of images as at least approximate point spread functions by determining an optical power where the point spread function is sharpest for at least three meridians, and calculating the refractive error based on the optical powers where the point spread function is sharpest determined for the at least three meridians.

17. A computer program wherein the computer program, when executed on a computing device, causes execution of the method of claim 16.

18. A method for producing a lens for spectacle glasses, the method comprising:
determining the refractive error of an eye according to the method of claim 16; an d producing the lens based on the determined refractive error.

19. A method for determining a refractive error of an eye, the method comprising:
capturing a series of images of light from the eye with varying optical power in a light path from the eye to a camera used for capturing the series of images; and
calculating the refractive error of the eye based on the series of images using the series of images as at least approximate point spread functions by determining an optical power where the point spread function is sharpest for at least three meridians, and calculating the refractive error based on the optical powers where the point spread function is sharpest determined for the at least three meridians,
wherein determining the optical powers where the point spread function is sharpest comprises calculating modulation transfer function areas for each of the at least three meridians; and
determining the optical power where the point spread function is sharpest as an optical power at a maximum modulation transfer function area for the respective meridian.

20. A kit comprising:
a computer program, wherein the computer program, when executed on a computing device, causes execution of a method for determining a refractive error of an eye, the method comprising:
capturing a series of images of light from the eye with varying optical power in a light path from the eye to a camera used for capturing the series of images; and
calculating the refractive error of the eye based on the series of images using the series of images as at least approximate point spread functions by determining an optical power where the point spread function is sharpest for at least three meridians, and calculating the refractive error based on the optical powers where the point spread function is sharpest determined for the at least three meridians; and
a hardware unit, the hardware unit including at least one element of the group consisting of:
an illumination device for illuminating the eye, and
an optical power changing device configured to vary the optical power of the light path from the eye to the camera.

* * * * *

UNITED STATES PATENT AND TRADEMARK OFFICE
CERTIFICATE OF CORRECTION

PATENT NO. : 11,944,383 B2
APPLICATION NO. : 18/450132
DATED : April 2, 2024
INVENTOR(S) : Nikolai Suchkov, Alexander Leube and Siegfried Wahl Page 1 of 1

It is certified that error appears in the above-identified patent and that said Letters Patent is hereby corrected as shown below:

In the Specification

In Column 3, Line 37: change "minor" to -- mirror --

In Column 5, Line 9: change "Homer" to -- Horner --

In Column 10, Line 49: change "that" to -- than --

In the Claims

In Column 14, Line 45, Claim 18: change "an d" to -- and --

Signed and Sealed this
Ninth Day of July, 2024

Katherine Kelly Vidal
*Director of the United States Patent and Trademark Office*